(12) United States Patent
Groll et al.

(10) Patent No.: US 9,308,343 B2
(45) Date of Patent: Apr. 12, 2016

(54) RESPIRATORY MASK WITH DISPOSABLE CLOTH BODY

(71) Applicant: Circadiance, LLC, Export, PA (US)

(72) Inventors: David Groll, Murrysville, PA (US); Ronnie E. Mahofski, North Huntingdon, PA (US); Nadine Scandinaro, Export, PA (US)

(73) Assignee: Circadiance, LLC, Turtle Creek, PA (US)

( * ) Notice: Subject to any disclaimer, the term of this patent is extended or adjusted under 35 U.S.C. 154(b) by 608 days.

(21) Appl. No.: 13/831,239

(22) Filed: Mar. 14, 2013

(65) Prior Publication Data

US 2014/0090649 A1    Apr. 3, 2014

Related U.S. Application Data

(63) Continuation-in-part of application No. 12/070,463, filed on Feb. 19, 2008, and a continuation-in-part of application No. 12/905,404, filed on Oct. 15, 2010, now abandoned.

(60) Provisional application No. 61/655,623, filed on Jun. 5, 2012.

(51) Int. Cl.
| | |
|---|---|
| *A61M 16/08* | (2006.01) |
| *A61M 16/06* | (2006.01) |
| *A61M 16/12* | (2006.01) |
| *A61M 16/00* | (2006.01) |

(52) U.S. Cl.
CPC ....... *A61M 16/0875* (2013.01); *A61M 16/0057* (2013.01); *A61M 16/06* (2013.01); *A61M 16/0683* (2013.01); *A61M 16/0694* (2014.02); *A61M 16/0816* (2013.01); *A61M 16/125* (2014.02); *A61M 16/0666* (2013.01); *A61M 2210/0618* (2013.01)

(58) Field of Classification Search
CPC ............ A61M 16/00; A61M 16/0048; A61M 16/06–16/0605; A61M 16/0616; A61M 16/0661; A62B 7/00–7/02; A62B 7/12; A62B 9/04; A62B 18/06–18/025; A41D 13/1161
See application file for complete search history.

(56) References Cited

U.S. PATENT DOCUMENTS

| | | | |
|---|---|---|---|
| 2,435,721 | A | 2/1948 | Lehmann |
| 2,641,253 | A | 6/1953 | Engelder |
| 3,357,426 | A | 12/1967 | Cohen |
| 3,750,665 | A | 8/1973 | Stranicky |

(Continued)

FOREIGN PATENT DOCUMENTS

| | | |
|---|---|---|
| AU | 2009215562 B2 | 2/2012 |
| FR | 2917296 A1 | 9/2006 |

(Continued)

*Primary Examiner* — Rachel Young
(74) *Attorney, Agent, or Firm* — The Ronald Law Group, LLC (57) ABSTRACT

The invention is a frameless, disposable cloth body for use with a respiratory mask, such as for continuous positive airway pressure therapy for those having sleep apnea. The cloth body is inflatable and moisture-vapor breathable and has an inner side having a nasal interface portion disposed on it and an outer side, and also has a circular aperture formed in a central location on the body, sized to sealingly receive an air delivery arrangement. The cloth body also has a pair of wings on opposite sides with slits arranged at optimal angles for receiving headgear straps.

25 Claims, 6 Drawing Sheets

(56) References Cited

U.S. PATENT DOCUMENTS

| | | | |
|---|---|---|---|
| 3,802,428 A | 4/1974 | Sherman | |
| 4,484,575 A | 11/1984 | Brockway | |
| 4,971,051 A | 11/1990 | Toffolon | |
| 5,243,971 A | 9/1993 | Sullivan | |
| 5,269,296 A | 12/1993 | Landis | |
| 5,429,126 A | 7/1995 | Bracken | |
| 5,431,158 A | 7/1995 | Tirotta | |
| 5,490,501 A | 2/1996 | Crowley | |
| 5,538,000 A | 7/1996 | Rudolph | |
| 5,728,451 A | 3/1998 | Langley | |
| 5,746,201 A | 5/1998 | Kidd | |
| 6,044,844 A | 4/2000 | Kwok | |
| 6,158,429 A * | 12/2000 | Gardner | A62B 17/04 128/201.22 |
| 6,269,814 B1 | 8/2001 | Blaszczykiewicz | |
| 6,338,340 B1 | 1/2002 | Finch | |
| 6,341,606 B1 | 1/2002 | Bordewick | |
| 6,357,440 B1 | 3/2002 | Hansen | |
| 6,510,818 B2 | 1/2003 | Barney | |
| 6,513,526 B2 | 2/2003 | Kwok | |
| 6,526,978 B2 | 3/2003 | Dominguez | |
| 6,634,358 B2 | 10/2003 | Kwok | |
| 6,698,427 B1 | 3/2004 | Clowers | |
| 6,701,927 B2 | 3/2004 | Kwok | |
| 6,763,835 B1 | 7/2004 | Grove | |
| 6,871,649 B2 | 3/2005 | Kwok | |
| 6,938,620 B2 | 9/2005 | Payne, Jr. | |
| 7,036,508 B2 | 5/2006 | Kwok | |
| 7,127,278 B2 | 10/2006 | Melker | |
| 7,159,587 B2 | 1/2007 | Drew | |
| 7,178,525 B2 | 2/2007 | Matula, Jr. | |
| 7,225,811 B2 | 6/2007 | Ruiz | |
| 7,347,229 B2 | 3/2008 | Glenn | |
| 7,406,966 B2 | 8/2008 | Wondka | |
| 7,481,220 B2 | 1/2009 | Meyer | |
| 7,481,221 B2 | 1/2009 | Kullik | |
| 7,779,832 B1 | 8/2010 | Ho | |
| 2002/0162556 A1 | 11/2002 | Smith | |
| 2003/0004445 A1* | 1/2003 | Hall | A61H 9/0078 601/41 |
| 2003/0131852 A1 | 7/2003 | Shafer | |
| 2003/0145857 A1 | 8/2003 | Sullivan | |
| 2005/0056286 A1* | 3/2005 | Huddart | A61M 16/06 128/206.21 |
| 2005/0061326 A1 | 3/2005 | Payne, Jr. | |
| 2005/0172968 A1 | 8/2005 | Hishida | |
| 2005/0199240 A1 | 9/2005 | Hall | |
| 2006/0027237 A1 | 2/2006 | Sleeper | |
| 2007/0131229 A1 | 6/2007 | Madaus | |
| 2007/0163595 A1 | 7/2007 | Chen | |
| 2007/0181135 A1 | 8/2007 | Baker | |
| 2007/0246043 A1 | 10/2007 | Kwok | |
| 2008/0047560 A1 | 2/2008 | Veliss | |
| 2008/0121235 A1 | 5/2008 | Ging | |
| 2008/0142015 A1 | 6/2008 | Groll | |
| 2008/0149104 A1 | 6/2008 | Eifler | |
| 2009/0065005 A1 | 3/2009 | Ades | |
| 2009/0107504 A1 | 4/2009 | McAuley | |
| 2009/0223518 A1 | 9/2009 | Kwok | |
| 2011/0253144 A1 | 10/2011 | Groll | |
| 2012/0055485 A1 | 3/2012 | Anthony | |

FOREIGN PATENT DOCUMENTS

| | | |
|---|---|---|
| GB | 2470172 B2 | 6/2011 |
| WO | WO0050121 A1 | 2/2000 |
| WO | WO2004037153 A3 | 10/2003 |
| WO | WO2005028010 A3 | 9/2004 |
| WO | WO2007136376 A1 | 11/2007 |

* cited by examiner

RESPIRATORY MASK WITH DISPOSABLE CLOTH BODY

CROSS-REFERENCE TO RELATED APPLICATIONS

This patent application is a continuation-in-part and claims priority from pending U.S. application Ser. No. 12/070,463, filed Feb. 19, 2008 and pending U.S. patent application Ser. No. 12/905,404, filed Oct. 15, 2010. This application also claims priority to Provisional Patent Application 61/655,623, filed Jun. 5, 2012. The entire specifications of all three applications are incorporated by reference herein.

FIELD OF THE INVENTION

The present invention relates, in general, to equipment used in the treatment of sleep apnea and other respiratory ailments and, more particularly, the instant invention relates to an improved nasal cloth body for an apparatus to deliver a fluid pressure to a patient in order to maintain the patient's airway open while sleeping and deliver oxygen to such patient.

BACKGROUND OF THE INVENTION

As is well known in the medical field, sleep apnea is a disorder that affects more than 12 million people in the United States alone. It takes its name from the Greek word apnea, which means "without breath." People with sleep apnea literally stop breathing repeatedly during their sleep, often for a minute or longer, and as many as hundreds of times during a single night.

Sleep apnea is known to be caused by either complete obstruction of the airway (obstructive apnea) or partial obstruction (obstructive hypopnea), both of which can cause the person suffering from such sleep apnea to wake up, temporarily, in order to breathe. There are three types of sleep apnea—obstructive, central, and mixed. Of these, obstructive sleep apnea (OSA) is the most common. OSA occurs in approximately 2 percent of women and 4 percent of men over the age of 35.

The exact cause of OSA remains unclear. The site of obstruction in most patients is the soft palate, extending to the region at the base of the tongue. There are no rigid structures, such as cartilage or bone, in this area to hold the airway open. During the day, muscles in the region keep the passage wide open. But as a person with OSA falls asleep, these muscles relax to a point where the airway collapses and breathing becomes impossible. When breathing stops, the sleeper partially awakens, involuntarily tenses the muscles in the region to open the airway in order to breathe, and falls back asleep. The arousal from sleep usually lasts only a few seconds, but these brief arousals disrupt continuous sleep and prevent the person from reaching the deep stages of slumber, such as rapid eye movement (REM) sleep, which the body needs in order to rest and replenish its strength. Even though normal breathing is restored when the person awakens briefly, the cycle is repeated throughout the night. Typically, the frequency of waking episodes is somewhere between 10 and 60, although a person with severe OSA may have more than 100 waking episodes in a single night.

Positive airway pressure has been demonstrated to be a very effective treatment for obstructive sleep apnea. It has three forms: continuous positive airway pressure (CPAP), autotitration, and bi-level positive airway pressure (BIPAP). While positive airway pressure is usually easier to tolerate at lower pressures, every patient requires a different pressure. In order to determine each individual patient's optimum airway pressure, it is necessary to titrate the pressure to each individual patient during a polysomnogram. A polysomnogram will show not only when the respiratory events have ceased, but also when the arousals from the respiratory events occur.

CPAP, the most common of the three therapy modes, is usually administered at bedtime through a facial mask held in place by straps around the patient's head. The mask is connected by a tube to a small air compressor about the size of a shoe box. The CPAP machine sends air under pressure through the tube into the mask, where, assuming a good seal with the patient's face, it applies a positive air pressure to the upper airways. This positive air pressure essentially "splints" the upper airway open and keeps it from collapsing.

Approximately 55 percent of patients who use CPAP do so on a nightly basis for more than four hours. The advantages of CPAP are that it is very safe and completely reversible. Generally, the treatment is well tolerated; however, it suffers from the disadvantage that it requires active participation every night; that is, the patient must put it on for it to work. If the mask is ill-fitting or causes unwanted side effects, compliance will not be maintained.

Nasal CPAP Masks on the market today fall into one of three design categories. They are either nasal masks, full face masks (i.e., those which cover the mouth and nose) or nasal pillows. The vast majority of CPAP masks that are currently on the market are comprised of a rigid plastic frame buffered by an elastomeric, rubbery "cushion" that makes the actual contact with the patient's face. These masks are sealed to the patient's face by tightening straps that hold the mask to the patient's head to increase mechanical pressure against and into the skin of the face. The skin and tissue of the patient's face is compressed by the mask, which forms a "gasket" that creates a seal and keeps the air pressure inside the mask elevated. Unfortunately, aside from being uncomfortable, a disadvantage to this approach is that the mechanical pressure applied to the patient's skin often exceeds the perfusion pressure in the tissue under the skin. Consequently blood flow to the tissue is diminished or cut off entirely. This leads to pain and can ultimately cause pressure sores on the patient's face. Additionally, it has been discovered that some of the masks, which use a silicone or a polyurethane gel to touch the face, have caused allergic reactions in some users.

These problems were largely overcome by the soft cloth mask disclosed in U.S. patent application Ser. No. 12/070,463 (the "'463 application"). The '463 application disclosed a nasal CPAP mask that was entirely comprised of a non-rigid, compliant material that had no fixed shaped unless breathable gas at positive pressure was flowing into it. While the nasal mask of the '463 application remedied many of the drawbacks with then-existing masks, it still occasionally suffered from air leakage at the interface between the patient's nose and the mask, due largely to the manner in which the nasal interface was constructed. The air leakage was a problem for many reasons, including, reduction of positive pressure applied to the patient's airway, dry eyes from air blowing into them, disruption of sleep of bed partner caused by both blowing jets of air and noise associated therewith.

The problems with air leakage in masks constructed in accordance with the '463 application were largely remedied by the introduction of the nasal interface disclosed in U.S. patent application Ser. No. 12/905,404 (the "'404 application"); however, there remained a small population of mask users who still experienced some difficulty in getting the mask to fit properly. When the previously disclosed mask was tightened on a user's face using the straps, the compliant material was occasionally stretched in a way that provided a less than optimal fit. Additionally, the mask of the '463 and '404 applications had a swivel connector that was affixed to the mask with tape, which made repeated cleaning of the mask challenging as re-taping the swivel to the inside of the mask required dexterity not possessed by all. Still further, the mask of the '463 and '404 applications included a headgear that connected to the mask from the top of the head, down across the forehead and between the eyes and to the bridge of the nose, which sometimes got in the way while the user was watching TV or reading a book. The mask of the '463 and '404 applications also included a swivel connector that allowed the air hose to rotate 360-degrees axially, but did not provide any angular freedom in that it only permitted the air hose to be directed downward away from the mask instead of providing the option to be directed sideways or upward toward the hairline of the user, for example. The present invention resolves the aforementioned problems.

SUMMARY OF THE INVENTION

It is, therefore, one of the primary objects of the present invention to provide a replaceable body portion, an improved nasal interface and headgear arrangement, an improved mechanism for detaching and attaching the swivel connector, a CPAP tube connector that allows 360° rotation of the tube to any placement preference of the user and a quieter exhalation system for an apparatus for communicating a positive fluid pressure to a patient's nasal and/or air passageways which has improved air sealing capability while still being more comfortable for the patient.

A further object of the present invention is to provide an apparatus for communicating a positive fluid pressure to a patient's nasal air passageways wherein substantially all portions of the apparatus that touch a patient's face are made of a stretchy, composite, moisture-vapor breathable material that is substantially capable of conforming to the patient's facial features and in which there are no rigid parts to press against the patient's skin In addition to the various objects and advantages of the present invention which have been described above, various other objects and advantages of the invention will become more readily apparent to those persons skilled in the relevant art from the following more detailed description of the invention, particularly, when such description is taken in conjunction with the attached drawing figures and with the appended claims.

DETAILED DESCRIPTION OF THE DRAWINGS

Prior to proceeding to the more detailed description of the instant invention it should be noted that identical components having identical functions have been designated with identical reference numerals throughout the several views illustrated in the drawings for the sake of clarity.

As used in the present specification and claims, the term "cloth body" means that portion of the mask that inflates as a result of the delivery of air from a pump through a tube with a swivel connector, including that portion that actually makes contact with the patient's nose and face when the CPAP mask is being used as intended.

As used in the present specification and claims, the term "compliant" means a material having very little rigidity such that it is easily bendable.

The term "inflatable" as used herein, means a material or a structure having two configurations: an uninflated configuration and an inflated configuration that is different from the uninflated configuration.

As used herein, the term "cloth" is meant to include natural and synthetic fiber cloth, treated cloth, laminates having a cloth base and cloth which is permeable or impermeable to air.

The Cloth Body

Figure 1:
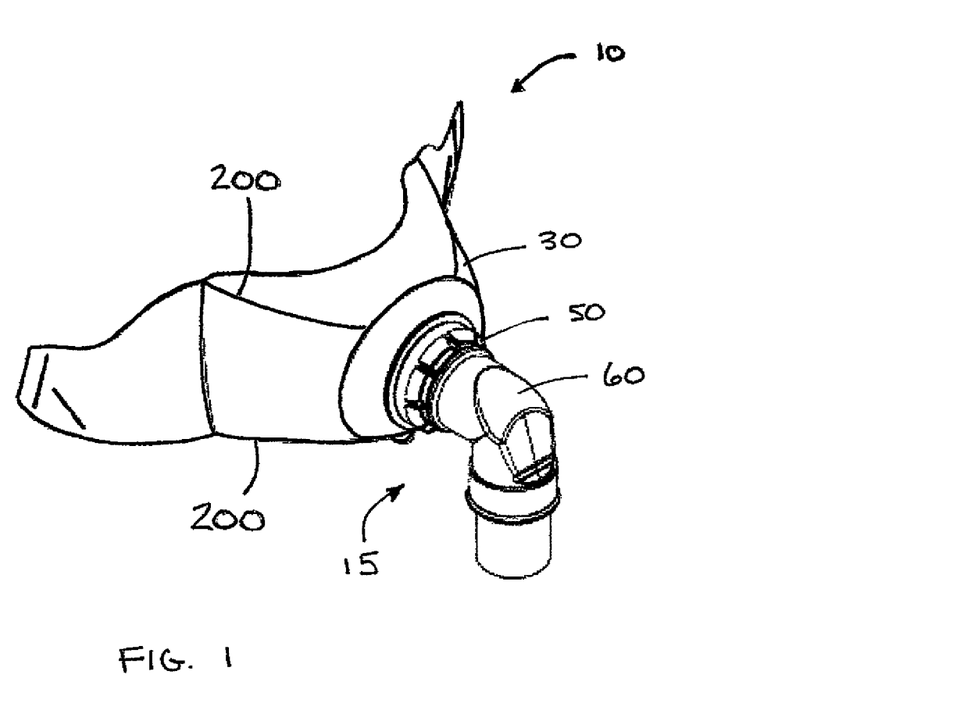
FIG. 1 is a perspective view of a CPAP mask of the present invention.
Figure 2:
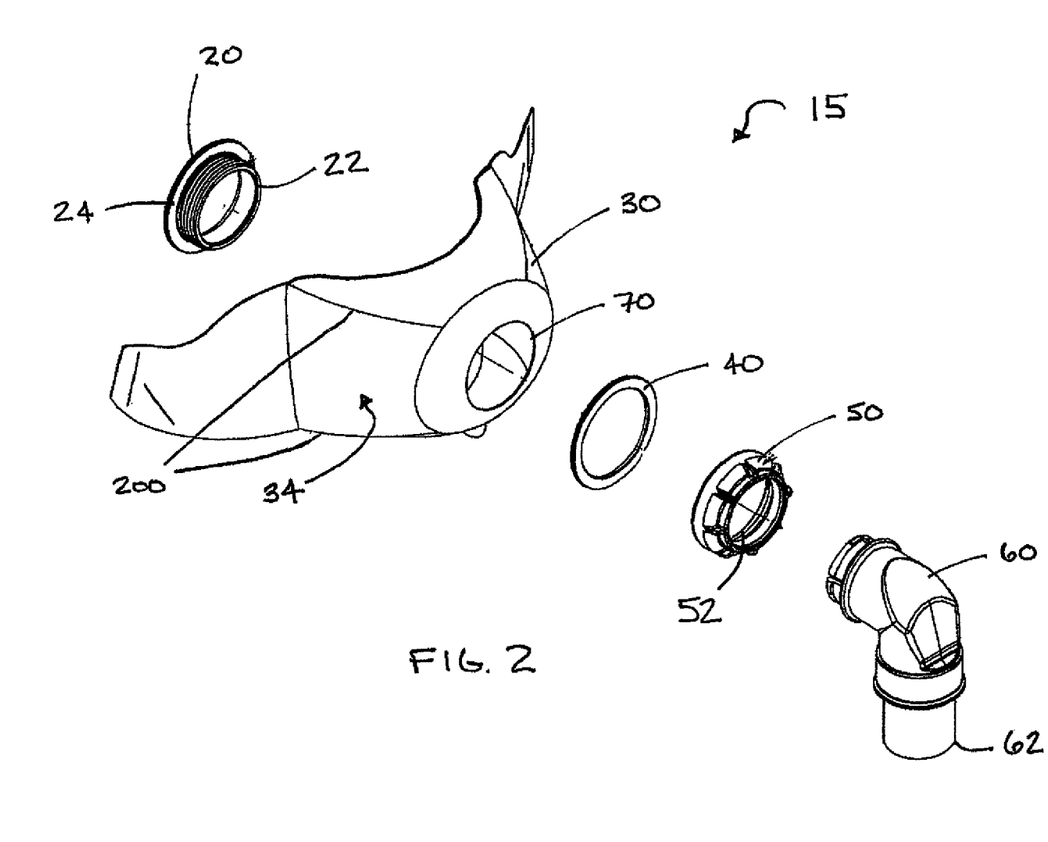
FIG. 2 is an exploded perspective view of the cloth body and air delivery arrangement of the present invention.

Referring now to FIGS. 1 and 2, a mask 10 of the present invention is illustrated fully assembled in FIG. 1 and in disassembled fashion in FIG. 2. Both figures illustrate a cloth body 30 and an air delivery arrangement 15. More specifically, FIG. 2 shows a swivel connector base portion 20, cloth body 30, washer 40, swivel connector clamping portion 50, and elbow 60 that combine to form the mask in an embodiment. While the swivel connector base portion 20 in the disclosed embodiment has a cylindrical projection 22 that is threaded to enable a tight connection with the connector clamping portion 50, which is matingly threaded on an interior portion 52, the washer 40 being insertable between the swivel connector base portion 20 and the clamping portion 50 to protect the cloth body material when the connector clamping portion is screwed onto the swivel connector base portion, and to form a more perfect airtight seal. As will be apparent to those of skill in the art, other means of connecting the clamping portion 50 and the base portion 20, such as a snap fit arrangement, can be used.

Generally, the cloth body 30 has an inner side 32, an outer side 34, and a pair of wings 80. Further, the inner side 32 includes a nasal interface portion 90 centrally disposed thereon. For assembly purposes, the cylindrical projection 22 is inserted through a circular aperture 70 formed in the cloth body 30, from the inner side 32, the aperture 70 having generally the same diameter as the cylindrical projection 22. A flange 24 keeps the base portion 20 from passing all the way through the aperture 70. As the flange 24 has generally the same outside diameter as the washer 40, connecting the swivel connector base portion 20 with the clamping portion 50 in the manner described, yields an airtight seal for air delivery into the cloth body from an air hose 220 that, when in operation, is connected to the outermost portion 62 of the elbow 60. Preferably, the elbow 60 comprises a three hundred sixty (360) degree swivel within the clamping portion 50 to permit an air hose 220 to be routed in multiple directions away from the cloth body 30. The outermost portion 62 also rotates axially within the elbow 60 to prevent the air hose 220 from kinking.

The cloth body 30 is frameless and does not have any rigid parts or aspects, nor does it need to be inserted into a rigid frame in order to work properly. Instead, it is comprised of soft, flexible, compliant materials that are light and flimsy, which is naturally more comfortable for the user than rubbery, rigid or molded masks. This design allows the cloth body 30 to have two distinct configurations: uninflated when not in use, and inflated when pressurized air is flowing through the mask, such was when therapy is being provided. Of course, the inflated configuration is different than the uninflated configuration. This composition also results in a mask that is much lighter than prior art masks. The following table illustrates the differences in weight between the present invention and other "lightweight" masks currently on the market:

| Weight Comparison | | | |
|---|---|---|---|
| | Present Invention | Resmed - Mirage FX ™ | Respironics - Easy Life ™ (Medium) |
| Mask & Headgear | 1.505 oz | 2.480 oz | 3.685 oz |
| Mask Only | .735 oz | 1.385 oz | 2.520 oz |
| Patient Interface | .140 oz | .795 oz | 1.505 oz |

The "patient interface" row in the above table provides a comparison between the weight of the cloth body as presently disclosed and the weights of those portions of the Mirage FX™ and Easy Life™ masks that touch the user's face, are replaceable, and which are generally described in the industry as "cushions". Thus, it is clear that the fully assembled mask and headgear of the present invention is nearly 40% lighter than the Mirage FX and less than half the weight of the Easy Life. The comparison of the masks and patient interfaces is even more striking. This reduction in weight means a more comfortable mask for the user, who has to wear it on their face a significant amount of time each night.

In a preferred embodiment, the majority of the cloth body 30, excluding the nasal interface portion 90, is comprised of an inelastic yet flexible composite material that is relatively impermeable to gas and is soft to touch. Preferably, this composite material is moisture-vapor breathable and comprised of a polyester cloth having a flexible coating such as a polyester or polyurethane film on the inner side 32.

The construction of the present invention, therefore, enables easy replacement of the used cloth body portion, while permitting re-use of the more durable hard plastic swivel connector base portion 20, washer 40, swivel connector clamping portion 50, and elbow 60, which reduces waste and shipping costs.

Figure 3:
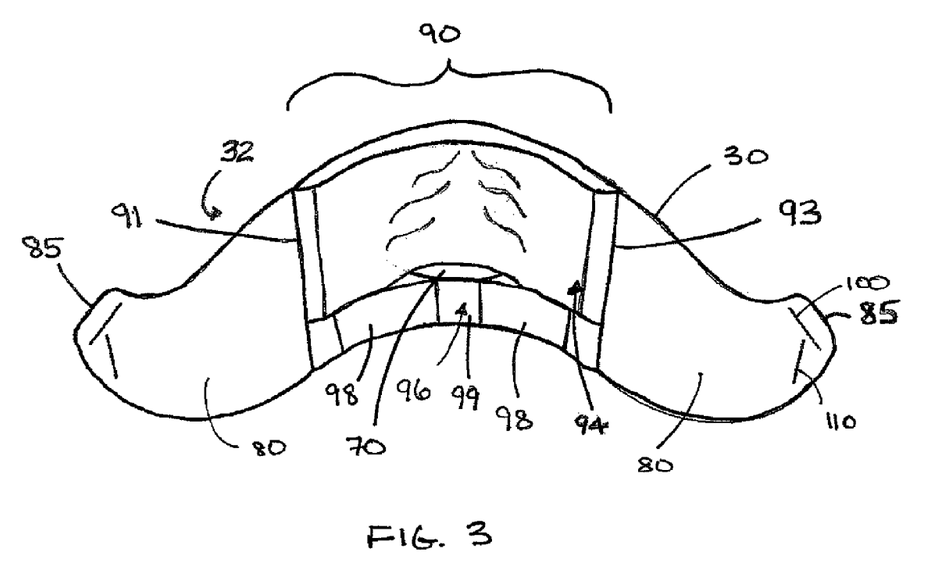
FIG. 3 is an illustration of the inner side of the cloth body illustrating the nasal interface portion of the present invention.
Figure 4:
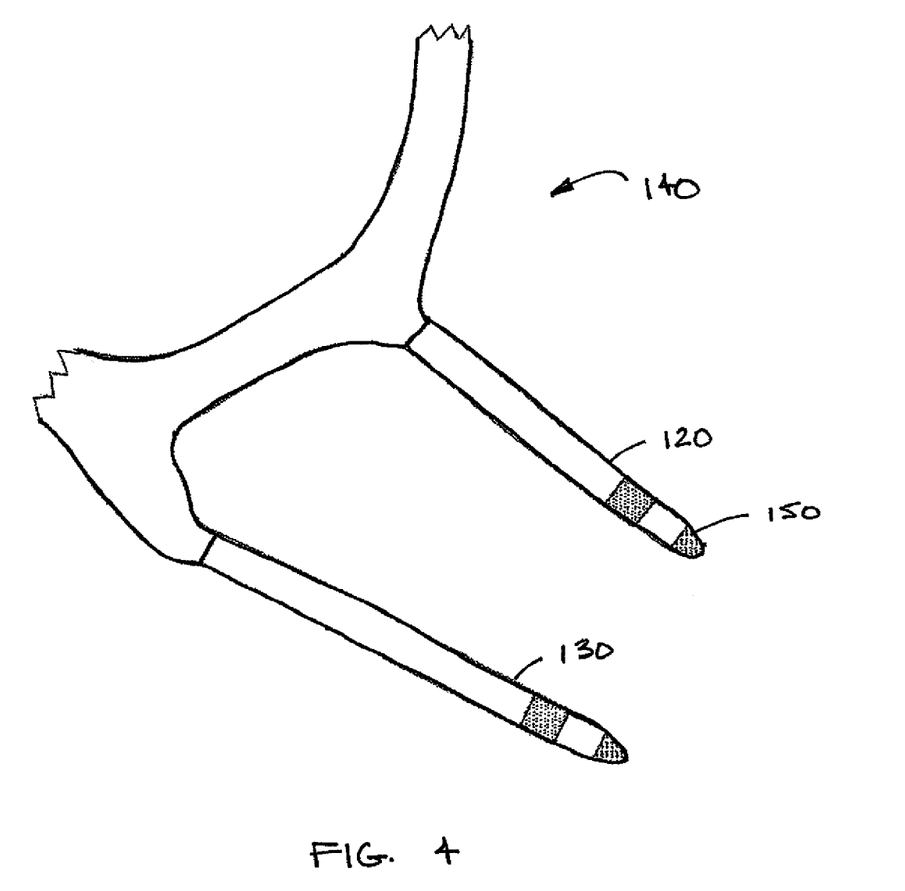
FIG. 4 is a cut-away portion of a headgear for use with the cloth body of the present invention.

Referring more specifically now to FIG. 3, the inner side 32 of the cloth body 30 is illustrated. In a preferred embodiment, a nasal interface portion 90 of the cloth body is designed to comfortably make contact with the nose and face of a user and is manufactured using an elastic moisture-vapor breathable material that is sewn or otherwise disposed onto the cloth body 30 from the inner side 32.

As used herein, the term "moisture-vapor breathable" refers to a fabric or other material that allows water vapor to pass through it from one side to the other. Moisture-vapor breathable materials are used because it has been shown that very small amounts of moisture within or under a mask can create the sensation of discomfort in a patient. Often, a mere 3% to 5% of increase in humidity is enough to create discomfort. If liquid water from sweating or exhalation cannot be dissipated quickly, as is the case with prior art nasal masks that use a silicone or polyurethane gel that contacts the skin, the humidity of the air in the space in between the skin and the cloth body rises. This increased humidity prevents rapid evaporation of liquid water on the skin and creates an increased sensation of heat, which, ironically, is what triggered the sweating in the first place. Consequently, the body responds with increased sweating to dissipate the excess thermal energy, which feeds into an unfortunate cycle of increased humidity and discomfort for the patient. The advantage of using a moisture-vapor breathable material, then, is that moisture and heat are wicked away from the skin as the cloth body is worn, which increases comfort, improves compliance, reduces heat, and reduces the moisture build-up at the cloth body contact area for the patient.

In a preferred embodiment, the elastic moisture-vapor breathable material used for the nasal interface portion 90 of the cloth body 30 of the present invention is a nylon and elastane (also referred to as Lycra®) combination with a polyurethane backing, which all together, is comprised of preferably seventy-two (72%) percent nylon (where the term nylon includes both the stretchy elastane and the nylon) and twenty-eight (28%) percent polyurethane. Further describing this preferred material, it weighs 138 grams per square meter, has waterproofness of 10,000 millimeters of water, and has tear strength of 18.4 Newtons×11.6 Newtons. Additionally, the moisture-vapor breathable material of the preferred embodiment has a moisture permeability of a range of approximately fifteen thousand to thirty-eight thousand (38,000) grams per meter squared per 24 hours using the Inverted Cup test JIS-L 1099 B-1.

In an alternative embodiment, the material used for the nasal interface portion 90 comprises fifty-six (56%) percent nylon, twenty-two (22%) percent elastane and twenty-two (22%) percent polyurethane. Further describing this material, it weighs 90 grams per square meter, has a moisture-vapor breathability transmission rate of 8,000 grams per meter squared per 24 hours using the ISO 15496 measurement method, a water proofness of greater than 10,000 millimeters of water using ISO 811 and has a breaking strength of 200 Newtons measured using the ISO 13934/1 test method. Other combinations of materials that accomplish the same task, however, will be apparent to those of skill in the art.

With continued reference to FIG. 3, the nasal interface portion 90 comprises at least a nose cradling portion 94 and an upper lip portion 96, each such portion having a first vertical edge 91 and a second vertical edge 93. The linear amount of material, measured laterally, from the first vertical edge 91 to the second vertical edge 93 is greater for the nose cradling portion 94 than for the upper lip portion 96 in order to comfortably and fittingly accommodate the patient's nose when the cloth body 30 is worn. The shape that is created by the combination of the nose cradling portion 94 and the upper lip portion 96, in conjunction with the elastic and stretchy quality of the material will cause it to naturally conform to the patient's nose as opposed to being stretched over the nose in an overly taut and uncomfortable manner. Additionally, the upper lip portion 96 has at least one wrapped section 98 that provides a soft contact point with the user's upper lip and is loosely and slidingly sleeved around an inner section 99, which provides a mechanism for increased width of the cloth body without sacrificing comfort. When the upper lip portion is stretched, such as with users with wider faces, the inner section becomes firmer than other portions of the mask and the wrapped section protects the user's upper lip against this firmness for additional comfort.

When the CPAP machine is turned on and the mask is in place on a user, the air pressure will build in the mask and inflate the cloth body 30 and, in conjunction with the headgear 140, cause the nasal interface portion 90 to gently and evenly push against the patient's skin to create the necessary seal. In this manner, it can be seen that the addition or removal of air pressure causes the cloth body to move between two different configurations: an uninflated configuration and an inflated configuration.

The Exhalation System

Figure 5:
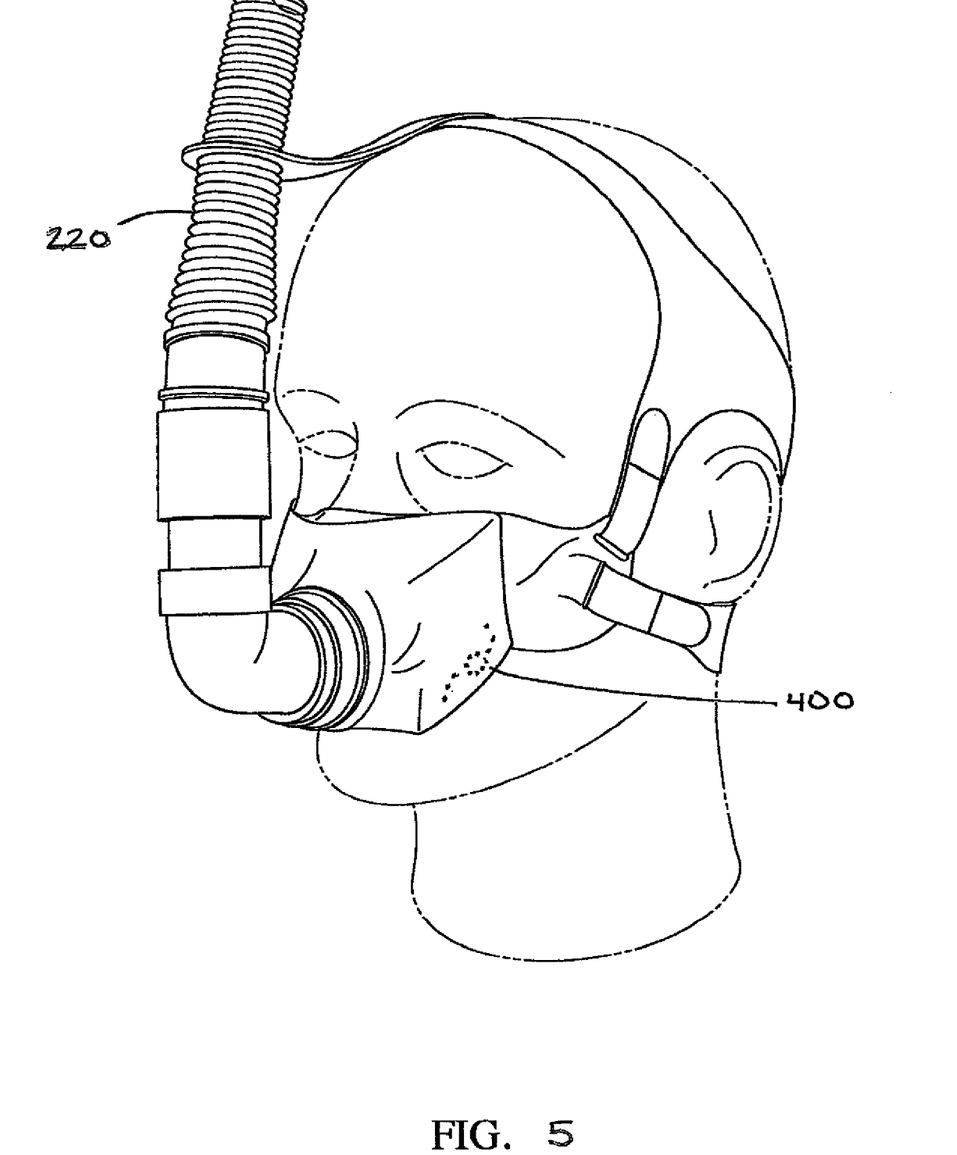
FIG. 5 is a perspective view of the CPAP mask and headgear of the present invention on the head of a patient.

A CPAP mask must have an exhalation system in order to facilitate the removal of carbon dioxide exhaled by the user. The cloth body 30 of the present invention has seams 200 where pieces of fabric have been stitched together with thread and these seams 200 function as part of the exhalation system in order to obtain an appropriate leak rate while still maintaining a minimal noise level so that the user's bed partner is not disturbed. Since each stitch is created by making a tiny hole in the fabric for the stitch and pulling the two separate pieces of fabric tightly together, the leak rate of a cloth body 30 can be modified by adjusting the length of fabric sewn together along with the number of stitches per inch to create the cloth body 30. In a preferred embodiment, then, it has been determined that the optimal leak rate is achieved through the use of between 6 and 30 stitches per inch over a seam length of between 16 and 22 inches in the cloth body 30, plus the use of a plurality of exhalation apertures 400. It has been discovered that the larger the cloth body, the longer the seams are and the fewer exhalation apertures are needed. So, in an embodiment for a large mask, a number of apertures in the range of 30 are necessary to provide the optimal exhalation rate for a given therapeutic pressure whereas a smaller mask requires more, such as a number in the range of 110 apertures, for the same therapeutic pressure and exhalation rate. In embodiments, the number of exhalation apertures can range from ten (10) to one hundred fifty (150) with each individual aperture being in a range of 0.004 and 0.006 inches in diameter. Further, while the exhalation apertures 400 illustrated in FIG. 5 are on the side of the cloth body, it is preferable that they be placed on the bottom to minimize the chance of any air being blown on a sleeping partner.

The Wings and Headgear

Referring now to FIGS. 3 through 6, wings 80 are laterally disposed on the body on both sides of the nasal interface portion 90 in order to connect the cloth body 30, and correspondingly the mask 10, to the headgear 140 to achieve the best fit possible. The wings each have a distal edge 85 and, in a preferred embodiment, an outer slit 100 disposed generally parallel to the distal edge 85 and an inner slit 110 tilted at an angle of approximately seventy (70) degrees from parallel with an upper terminus of the inner slit 110 being closer to the outer slit 100 than a lower terminus of the inner slit 110. The purpose of the slits 100, 110 is to slidingly receive a first headgear strap 120 and a second headgear strap 130 on a headgear 140 in order to provide the best possible fit without compromising the seal. In a preferred embodiment both headgear straps have hook and loop fastening systems 150 disposed thereon for ease of adjustment as is well-known in the art.

The wings 80 are made of a heavier material than the rest of the cloth body and can be manufactured with polyurethane foam coated with a nylon, by way of example, or in an alternative embodiment, can be reinforced by doubling up the material used for the body. In one embodiment, two pieces of composite material used for the body are heated at four hundred twenty-five (425) degrees for 7 seconds with a pressure setting of 7 on a George Knight DK-76 Heat Press so that they are heat welded together and the resulting heat welded material is use for the wings. As will be apparent to those of skill in the art, other means of bonding and/or other process settings can be used to bond two pieces of fabric. With this stronger material, the wings do not collapse or fold when the headgear straps are tightened by the user. The stronger material also has the effect of decentralizing pressure points and optimizing fit.

When worn, the first headgear strap 120 is slid by the user through the outer slit 100 and the second headgear strap 130 is slid through the inner slit 110 and both headgear straps are then adjusted until the user is comfortable. The angles of the slits have been intentionally chosen so that the first headgear strap 120 that is slid through the outer slit 100 substantially controls the vertical height of the mask on the user's face; whereas the second headgear strap 130 that is fed through the inner slit 110 substantially controls the tightness of the mask on the user's face. The hook and loop fastening system is color coded to ensure both headgear straps are placed in the appropriate slits. In embodiments, different headgear strap sizes may also be used to ensure they are inserted through the appropriate slits. The headgear is designed so the headgear straps curve above and below the ear in order to maintain maximum comfort and provide optimum nasal mask support. Additionally, the wings 80 are curved to ensure the wearer's eyes are not covered or interfered with.

Figure 6:
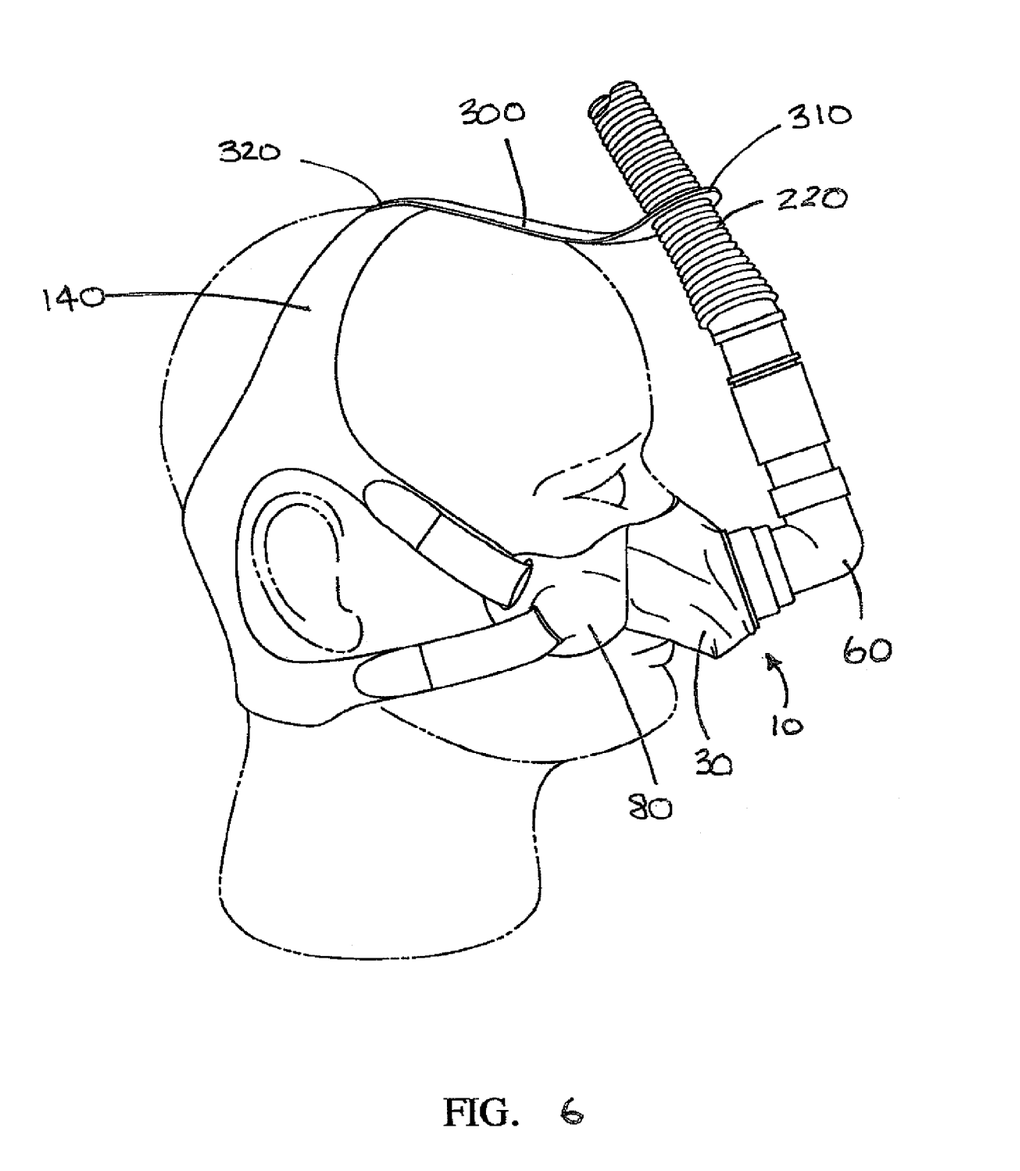
FIG. 6 is a perspective view of the CPAP mask and headgear of the present invention on the head of a patient.

Surprisingly, this headgear 140 eliminates the need for a strap that travels from the top of the mask, up the bridge of the nose and between the eyes to the top of the head, thus increasing the types of activities a wearer can comfortably participate in while undergoing treatment, but before falling asleep. Once the wearer decides to go to sleep, however, a tether strap 300 can be attached to the air hose 220 at a first end 310 and removably disposed on the headgear 140 at a second end 320 in order to allow the patient to have the tube placed directly over their head while sleeping, if desired. In a preferred embodiment, the tether strap 300 has sufficient rigidity to keep the air hose 220 from touching the user's face while he or she is sleeping on their back and also has a hole formed therein that is slightly smaller than the air hose 220 at the first end 310 so that the air hose 220 can be frictionally held stationary in relation to the tether strap 300. In an embodiment, the tether strap is comprised of polyurethane foam coated with a nylon and lycra combination and is attached to the headgear via a hook and loop fastening system.

If not otherwise stated herein, it is to be assumed that all patents, patent applications, patent publications and other publications (including web-based publications) mentioned and cited herein are hereby fully incorporated by reference herein as if set forth in their entirety herein.

While in accordance with the patent statutes the presently preferred and various alternative embodiments of the instant invention have been described in detail above, it should be understood that various other modifications and alternatives can be envisioned by those persons skilled in the art without departing from either the spirit of the invention or the scope of the appended claims.

What is claimed is:

1. A frameless inflatable respiratory mask comprising:
a cloth body having a circular aperture, an inner side and an outer side, the inner side having a nasal interface portion disposed thereon; the nasal interface portion comprising an upper lip portion having an inner section and at least one wrapped inelastic section loosely sleeved around the inner section; the body further having a pair of wings disposed on opposite sides laterally; an air delivery arrangement adapted to sealingly deliver air through the circular aperture; an exhalation system disposed on the mask; and a headgear for securing and adjusting the mask on a user's head adjustably disposed on the wings; whereby air that is delivered to the mask via the air delivery arrangement inflates the cloth body to enable air to be delivered at a therapeutic pressure.

2. The frameless inflatable respiratory mask of claim 1, wherein the cloth body is manufactured with an inelastic yet flexible material.

3. The frameless inflatable respiratory mask of claim 2, wherein the wings are comprised of two layers of the material.

4. The frameless inflatable respiratory mask of claim 2, wherein the wings are comprised of a heavier material that is thicker than the inelastic yet flexible material.

5. The frameless inflatable respiratory mask of claim 2, wherein the material is a polyester cloth.

6. The frameless inflatable respiratory mask of claim 2, wherein the material has an impermeable to air coating.

7. The frameless inflatable respiratory mask of claim 6, wherein the coating is either a polyester film or a polyurethane film.

8. The frameless inflatable respiratory mask of claim 1, wherein the cloth body shape is created by sewing the body together with thread, the sewing creating seams in the body.

9. The frameless inflatable respiratory mask of claim 1, wherein the cloth body has a first uninflated configuration and a second inflated configuration different than the first uninflated configuration.

10. The frameless inflatable respiratory mask of claim 1, wherein the nasal interface portion is manufactured with an elastic moisture-vapor breathable material.

11. The frameless inflatable respiratory mask of claim 10, wherein the elastic moisture-vapor breathable material is a combination of nylon, elastane and polyurethane.

12. The frameless inflatable respiratory mask of claim 1, wherein the nasal interface portion further comprises a nose-cradling portion wherein the amount of material measured laterally is greater than the amount of material used for the upper lip portion.

13. The frameless inflatable respiratory mask of claim 1, wherein the air delivery arrangement is removably sealed to the cloth body.

14. The frameless inflatable respiratory mask of claim 1, wherein the air delivery arrangement is sealed to the cloth body with a threaded projection that passes from the inner side through the aperture and connects to a clamping portion on the outer side.

15. The frameless inflatable respiratory mask of claim 1, wherein the exhalation system comprises a plurality of apertures in the cloth body.

16. The frameless inflatable respiratory mask of claim 15, wherein the exhalation system further comprises seams.

17. The frameless inflatable respiratory mask of claim 1, wherein the headgear further comprises a tether strap with a first end disposed on the headgear and a second end forming an aperture to frictionally receive an air hose therethrough, the strap being of sufficient rigidity to keep the air hose at least a predetermined distance away from the user's face.

18. The frameless inflatable respiratory mask of claim 1, wherein the wings each have a distal edge, each distal edge having a plurality of slits formed therein for receiving headgear straps.

19. The frameless inflatable respiratory mask of claim 18, wherein the plurality of slits include an outer slit oriented parallel to each distal edge for receiving an upper strap and an inner slit adjacent to each outer slit, oriented at an angle to each outer slit to receive a lower strap.

20. The frameless inflatable respiratory mask of claim 19, wherein the angle is substantially seventy degrees.

21. The frameless inflatable respiratory mask of claim 18, wherein the headgear straps are adapted to curve around the ear and the wings are adapted to curve under the eyes to be more comfortable for the user.

22. The frameless inflatable respiratory mask of claim 1, wherein the headgear further comprises a tether strap having sufficient stiffness to keep an air hose substantially away from the user's face during CPAP therapy.

23. A disposable body for a respiratory mask comprising a cloth body having an inner side, an outer side, the cloth body forming a circular aperture sized to sealingly receive an air delivery arrangement; a pair of wings disposed on opposite lateral sides of the body for receiving headgear straps; and a nasal interface portion disposed on the inner side of the cloth body for securely cradling a nose of a user, the nasal interface portion comprising an upper lip portion having an inner section and at least one wrapped inelastic section loosely sleeved around the inner section.

24. A kit comprising:
one or more disposable cloth bodies having an inner side, an outer side, an aperture formed in the one or more bodies, a pair of wings disposed on opposite lateral sides of the one or more bodies for receiving headgear straps; and a nasal interface portion disposed on the inner side of the one or more cloth bodies for securely cradling a nose of a user, the nasal interface portion comprising an upper lip portion having an inner section and at least one wrapped inelastic section loosely sleeved around the inner section, and packaging capable of housing one or more of the one or more cloth bodies.

25. A method of delivering air at a therapeutic pressure to a user comprising:
providing a respiratory mask having cloth body forming a circular aperture, an inner side, and an outer side, the inner side having a nasal interface portion disposed thereon, the nasal interface portion comprising an upper lip portion having an inner section and at least one wrapped inelastic section loosely sleeved around the inner section, the body further having a pair of wings disposed on opposite sides laterally, an air delivery arrangement adapted to sealingly deliver air through the circular aperture; an exhalation system disposed on the mask, and a headgear for securing and adjusting the mask on a user adjustably disposed on the wings; whereby air that is delivered to the mask via the air delivery arrangement inflates the cloth body to enable air to be delivered at a therapeutic pressure;
securing the respiratory mask to the user such that the respiratory mask covers a nose of the user; and
delivering air to the user via the mask.

* * * * *